United States Patent [19]

Ogawa et al.

[11] Patent Number: 4,626,101
[45] Date of Patent: Dec. 2, 1986

[54] SURFACE DEFECT INSPECTING APPARATUS

[75] Inventors: Shigeru Ogawa, Yokohama; Hiroshi Yamaji, Chigasaka; Masaaki Kano, Kamakura, all of Japan

[73] Assignee: Kabushiki Kaisha Toshiba, Kawasaki, Japan

[21] Appl. No.: 675,008

[22] Filed: Nov. 26, 1984

[30] Foreign Application Priority Data

Nov. 26, 1983 [JP] Japan .................................. 58-221394
Jul. 19, 1984 [JP] Japan .................................. 59-148614

[51] Int. Cl.$^4$ .......................................... G01N 21/89
[52] U.S. Cl. .................................... 356/237; 250/563; 356/236
[58] Field of Search ....................... 356/236, 237, 446; 250/563, 572

[56] References Cited

U.S. PATENT DOCUMENTS

| | | | |
|---|---|---|---|
| 4,360,275 | 11/1982 | Louderback | 356/446 |
| 4,376,583 | 3/1983 | Alford et al. | 356/237 |
| 4,378,159 | 3/1983 | Galbraith | 356/237 |
| 4,391,524 | 7/1983 | Steigmeier et al. | |
| 4,428,672 | 1/1984 | Allard et al. | 356/237 |
| 4,441,124 | 4/1984 | Heebner et al. | 356/237 X |

FOREIGN PATENT DOCUMENTS 0065051 11/1982 European Pat. Off. .
57-163852 10/1982 Japan .

Primary Examiner—Davis L. Willis
Assistant Examiner—Matthew W. Koren
Attorney, Agent, or Firm—Cushman, Darby and Cushman

[57] ABSTRACT

The holding mechanism holds an object under inspection in a manner that the substantially entire surface of the object may relatively be scanned by a laser beam. A spherical integrating light collector has an opening disposed close to the inspected surface of the object held by the holding mechanism. A laser beam illuminating mechanism is coupled with the other end of the spherical integrating light collector, and illuminates the inspected surface of the object with the laser beam through the opening. A photo-electric converter receives the scattered light as is reflected by the inspected surface and collected by the spherical integrating light collector, and converts the scattered light into an electrical signal representing an amount of light. An analog to digital converter converts the electrical signal derived from the photo-electric converter into a digital signal. A peak detector receives the digital signal derived from the analog to digital converter to detect peak values at predetermined periods. A mean value calculator calculates a mean value using a digital signal output from the analog to digital converter. A reference value storing memory stores a reference value to determine defects present on the inspected surface of the object. A threshold level calculator calculates the threshold level using the reference value and the mean value. A defect detector compares peak values derived from the peak detector with the threshold level, and detects the surface defects on the basis of the result of the comparison.

19 Claims, 19 Drawing Figures

FIG. 7

TRACKING POSITION →

|   | 1 | 2 | -------- | 100 |
|---|---|---|---|---|
| 1 | $Y_1, 1$ | $Y_2, 1$ | -------- | $Y_{100}, 1$ |
| 2 | $Y_1, 2$ | $Y_2, 2$ | -------- | $Y_{100}, 2$ |
| ⋮ | ⋮ | ⋮ | -------- | ⋮ |
| 360 | $Y_1, 360$ | $Y_2, 360$ | -------- | $Y_{100}, 360$ |

ROTATING POSITION ↓

FIG. 8

TRACKING POSITION →

|   | 1 | 2 | -------- | 10 |
|---|---|---|---|---|
| 1 | $Z_1, 1$ | $Z_2, 1$ | -------- | $Z_{10}, 1$ |
| 2 | $Z_1, 2$ | $Z_2, 2$ | -------- | $Z_{10}, 2$ |
| ⋮ | ⋮ | ⋮ | -------- | ⋮ |
| 360 | $Z_1, 360$ | $Z_2, 360$ | -------- | $Z_{10}, 360$ |

ROTATING POSITION ↓

| | TRACKING POSITION → | | | |
|---|---|---|---|---|
| | 1 | 2 | ------ | n |
| 1 | X₁,1 | X₂,1 | ----- | Xn,1 |
| 2 | X₁,2 | X₂,2 | ----- | Xn,2 |
| 3 | X₁,3 | X₂,3 | ----- | Xn,3 |
| 4 | X₁,4 | X₂,4 | ----- | Xn,4 |
| 5 | | | ----- | |
| 6 | | | ----- | |
| ⋮ | | | | |
| 358 | X₁,358 | | | |
| 359 | X₁,359 | | | |
| 360 | X₁,360 | | ----- | Xn,360 |

$1 \leq \theta \leq 360$

ROTATING POSITION ←

SURFACE DEFECT INSPECTING APPARATUS

BACKGROUND OF THE INVENTION

This invention relates to an apparatus for inspecting an object for defects on the surface thereof, and more particularly to an apparatus for inspecting a semiconductor wafer for defect or defects, for example, contamination, dust, scratches, etc. on the wafer surface.

In manufacturing semiconductor devices, it is an essential step to inspect silicon wafers for semiconductor devices as to whether or not there are scratches, dust or contamination shown on the surface of the semiconductor devices. For the inspection, a skilled person visually checks the surface of the semiconductor wafer to find the surface defect.

In the case of the visual inspection, however, the results of the inspections usually differ with inspecting persons. Therefore, the inspection results can not be used for quantitativing the results to find or detect defect or defects on the wafer surface. The recent integrated circuits have been miniaturized in size more and more, and actually it is required to discriminate 1 μm or less of the surface defect size for exact evaluation of the semiconductor manufacturing process. It is impossible, however, to discriminate such a minute size by a visual inspection.

To cope with this problem, there has been developed and marketed another surface defect inspection apparatus using the reflecting light. In the apparatus, the surface of a semiconductor wafer is illuminated with light beam 3 from an incandescent light source or a laser source, as shown in FIG. 1. A regular reflecting light 4 and the scattered light 5 are sensed by photo-electric converters 6 and 6. The output voltages from the photo-electric converters 6 and 6 are compared with one or more threshold voltages to detect defect, e.g., contamination, dust, or scratch on the wafer surface, and to discriminate the size of the defect.

In the conventional surface defect inspecting apparatus, a fixed threshold level $V_T$ is set up for the defect detection. Different wafers under inspection provide different output signal levels, respectively. For example, as shown in FIG. 2, a semiconductor wafer with a mirror surface produces an output signal $V_I$. A film formed wafer provides an output signal $V_{II}$. Therefore, the threshold level must be changed for each wafer under inspection, and the threshold level must be experimentally determined. The setting of the threshold level is troublesome and time-consuming work. In the case of a warped semiconductor wafer, the same problem arises. The sizes of defects as detected and classified can not be used for quantitative processing purposes. Therefore, it is necessary to calibrate the defect size data by a reference sample every time the data are collected.

SUMMARY OF THE INVENTION

It is, therefore, an object of the present invention to provide a new and improved apparatus which quantitatively, quickly and accurately inspects an object for defects on the surface thereof, without experimentally setting up threshold levels or calibrating the collected data of surface defects.

According to the present invention, there is provided an apparatus for inspecting an object under inspection for defects on the surface thereof, comprising means for holding the object under inspection in a manner that the substantially entire surface of the object may relatively be scanned by laser beam, spherical integrating light collecting means provided at one end with an opening as is disposed close to the inspected surface of the object held by the holding means, laser beam illuminating means coupled with other end of the spherical integrating light collecting means and for illuminating the inspected surface of the object with the laser beam through the opening, photo-electric converting means for receiving the scattered light as is reflected by the inspected surface and collected by the spherical integrating light collecting means, and for converting the scattered light into an electrical signal representing an amount of light, analog to digital converting means for converting analog to digital the electrical signal derived from the photoelectric converting means into a digital signal, peak detecting means for receiving the digital signal derived from the analog to digital converting means to detect peak values at predetermined periods, means for calculating a mean value based on a digital signal output from the analog to digital converting means, means for storing at least one reference value which is for determining at least one threshold level to detect surface defect or defects present on the inspected surface, means for calculating the threshold level based on the reference value and the mean value, and surface defect detecting means for comparing peak values derived from the peak detecting means with the threshold level, and for detecting the surface defect or defects depending on the result of the comparison.

BRIEF DESCRIPTION OF THE DRAWINGS

The present invention can be understood by reference to the accompanying drawings, in which:

FIG. 7 maps an arrangement of data stored in a temporary memory of the FIG. 3 embodiment;

FIG. 8 maps an arrangement of defect data for each picture element stored in a data memory of the FIG. 3 embodiment;

DETAILED DESCRIPTION OF THE PREFERRED EMBODIMENTS

The present invention will be described in detail using some specific embodiments with reference to the accompanying drawings.

Figure 1:
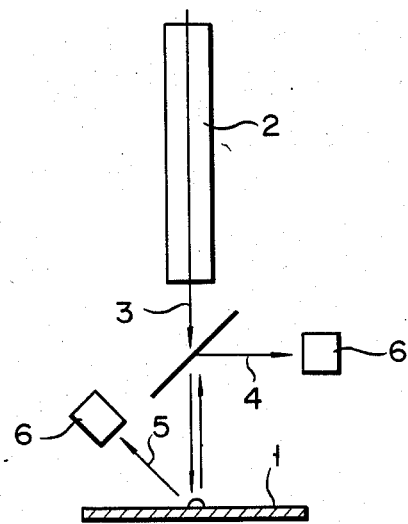
FIG. 1 schematically shows a prior apparatus for inspecting an object under inspection on defects on the surface thereof.
Figure 2:
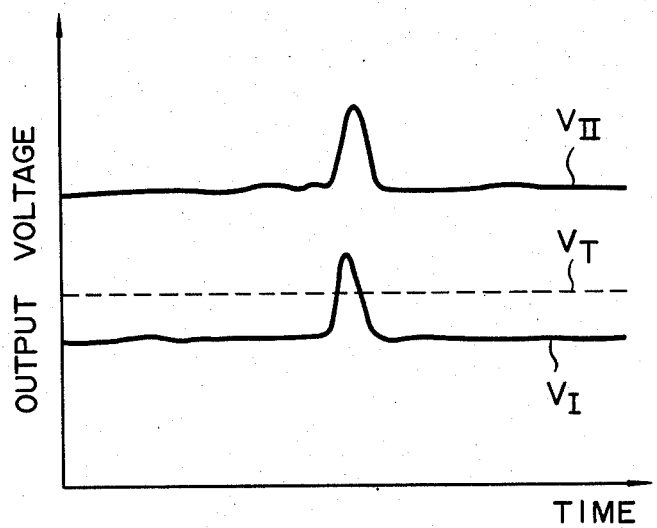
FIG. 2 is a graph for graphically explaining a disadvantage of the surface inspecting apparatus of FIG. 1.
Figure 3:
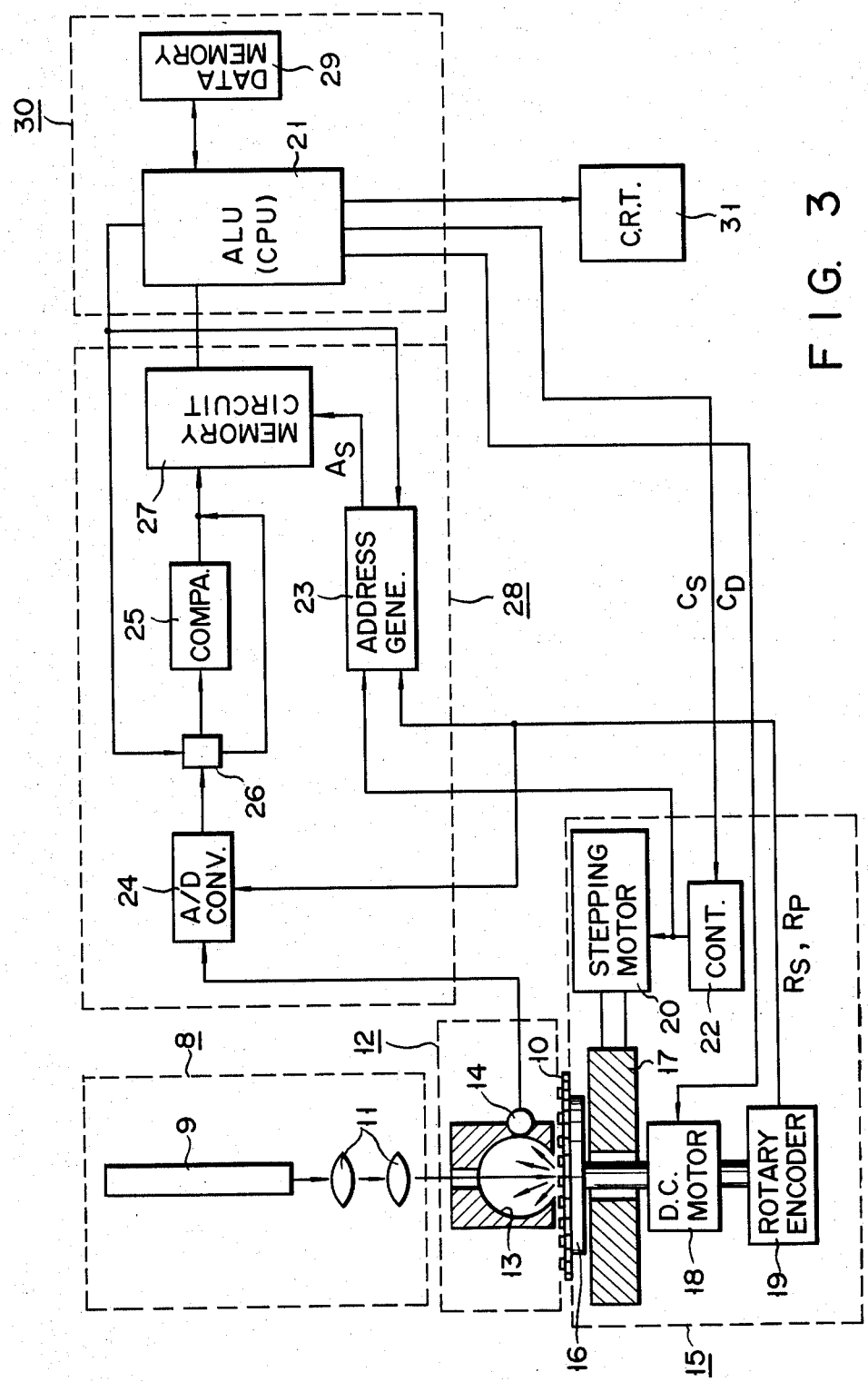
FIG 3 shows in block form an overall circuit arrangement of a surface defect inspecting apparatus which is an embodiment according to the present invention.

Reference is made to FIG. 3 illustrating a first embodiment of an apparatus for inspecting an object under inspection, for example, a semiconductor wafer, for defect or defects on the surface thereof (referred to as a surface defect inspecting apparatus). In the figure, an illuminating section 8 is comprised of a laser source 9, and a lens system 11 for optically processing laser beams generated from the laser source 9 and spotting the surface of an object 10 with the laser beam. A photo sensing section 12 located right under the illuminating section 8 includes a spherical integrating light collector 13 and a photo-electric converter 14 buried in the light collector 13. The light collector 13 is used for collecting rays of light scattered by defects on the surface of the object 10, and has a spherical inner surface scattering made of magnesium oxide, for example. The object 10 is removably placed on a turntable 16 as a part of a scanning section 15 by a means (not shown), for example, a vacuum chuck. The photo-electric converter 14 converts the collected scattered light into an electric signal, and may be a photo multiplier, a photo transistor, a photo diode, or the like. The turntable 16 is comprised of a DC motor 18 directly coupled with the turntable 16 for its rotation, a rotary encoder 19 for producing a rotation start signal Rs and a rotating position signal Rp, which are for the turntable 16 and a stepping motor 20 for radially moving the turntable 16 track by track, as will be given later. The DC motor 18 and the stepping motor 20 are driven under control of control signals derived from a operation control unit 21 installed separately from the scanning section 15. Through the operation of the motors, the entire surface of the object 10 is coaxial scanned by the laser beam. The stepping motor 20 is connected to the operation control unit 21, through a stepping motor control circuit 22. The rotary encoder 19 is connected to an address generating circuit 23 and an analog to digital (A/D) converter 24. The A/D converter 24 converts the output voltage signal output from the photo-electric converter 14 in the photo sensing section 12 into a digital signal. The output of the A/D converter 24 is connected to the input of a comparator 25 through a by-path circuit 26 made up of a switching element. The comparator 25 compares between the digital signals converted at every consecutive ten points, and successively produces maximum values, or peak values, of the compared ones. The output of the comparator 25 is connected to a memory circuit 27 for scattered light data. The input of the memory circuit 27 is connected to the output of the address generating circuit 23 for storing the scattered light data corresponding to a rotation and a moving position of the turntable 16. The input of the address generating circuit 23, together with the rotary encoder 19, is connected to the output of the stepping motor control circuit 22. The output of the A/D converter 24 is connected to the input of the memory circuit 27, by way of the by-path circuit 26. The address generating circuit 23, the A/D converter 24, the comparator 25, the by-path circuit 26, and the memory circuit 27 make up a temporary memory 28.

The memory circuit 27 is connected to the control unit 21 made up of a microcomputer, for example, and is controlled by the operation control unit 21 for reading and writing of data. The operation control unit 21 is connected to the by-path circuit 26, the address generating circuit 23, the DC motor 18 and the stepping motor control circuit 22, and supplies control signals to these circuits. The operation control unit 21 is connected to a data memory 29 for storing a program for data processing and the sizes of defects as classified. The data memory 29, together with the operation control unit 21, forms a data processing unit 30. The operation control unit 21 is connected to a display section 31 including a cathode ray tube (CRT) for visually displaying a distribution of defects on the surface of the object 10 and the number of defects as classified for each size.

Figure 4A:
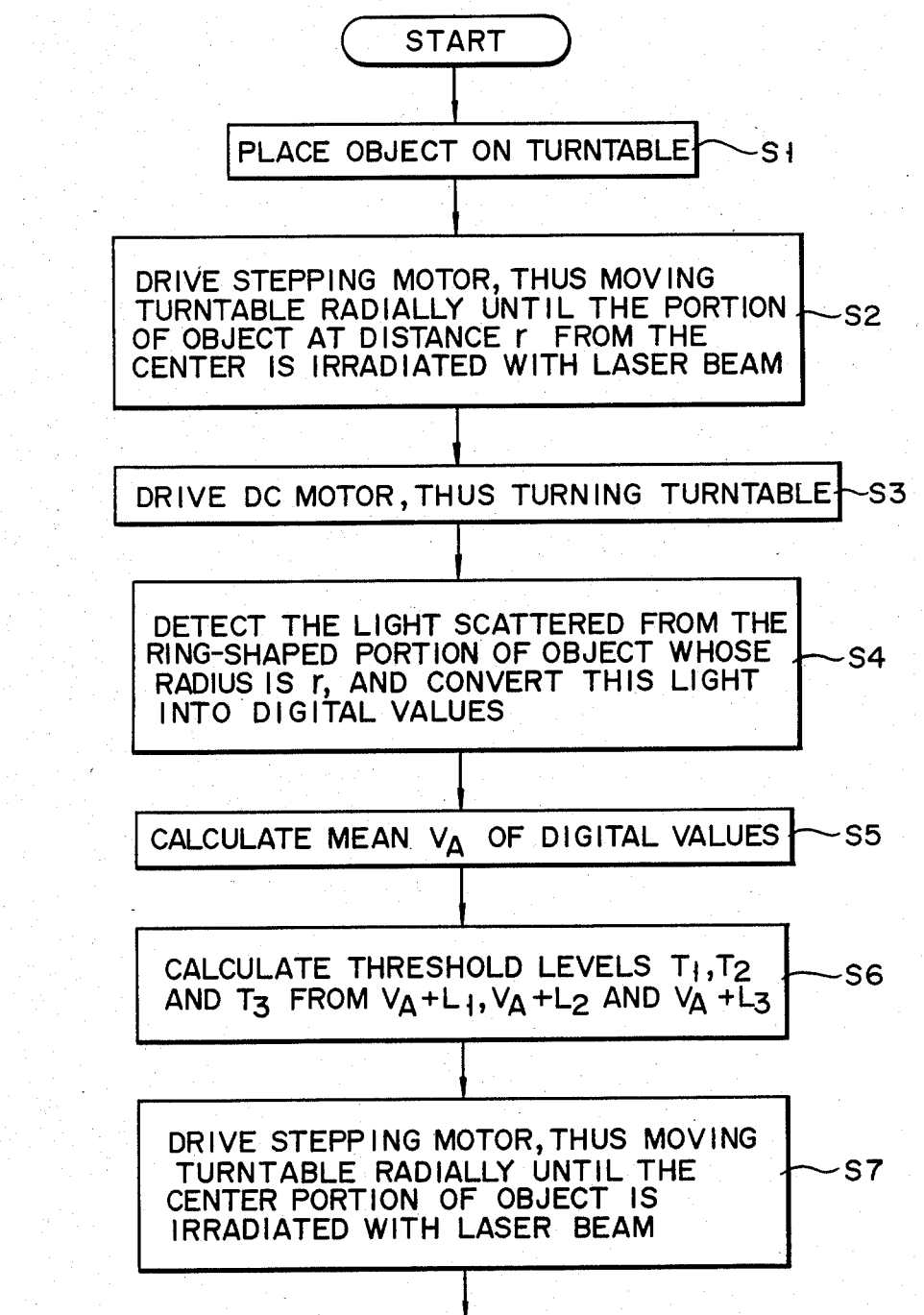
FIGS. 4A and 4B chart flow of the operations of the surface defect inspecting apparatus of FIG. 3.
Figure 4B:
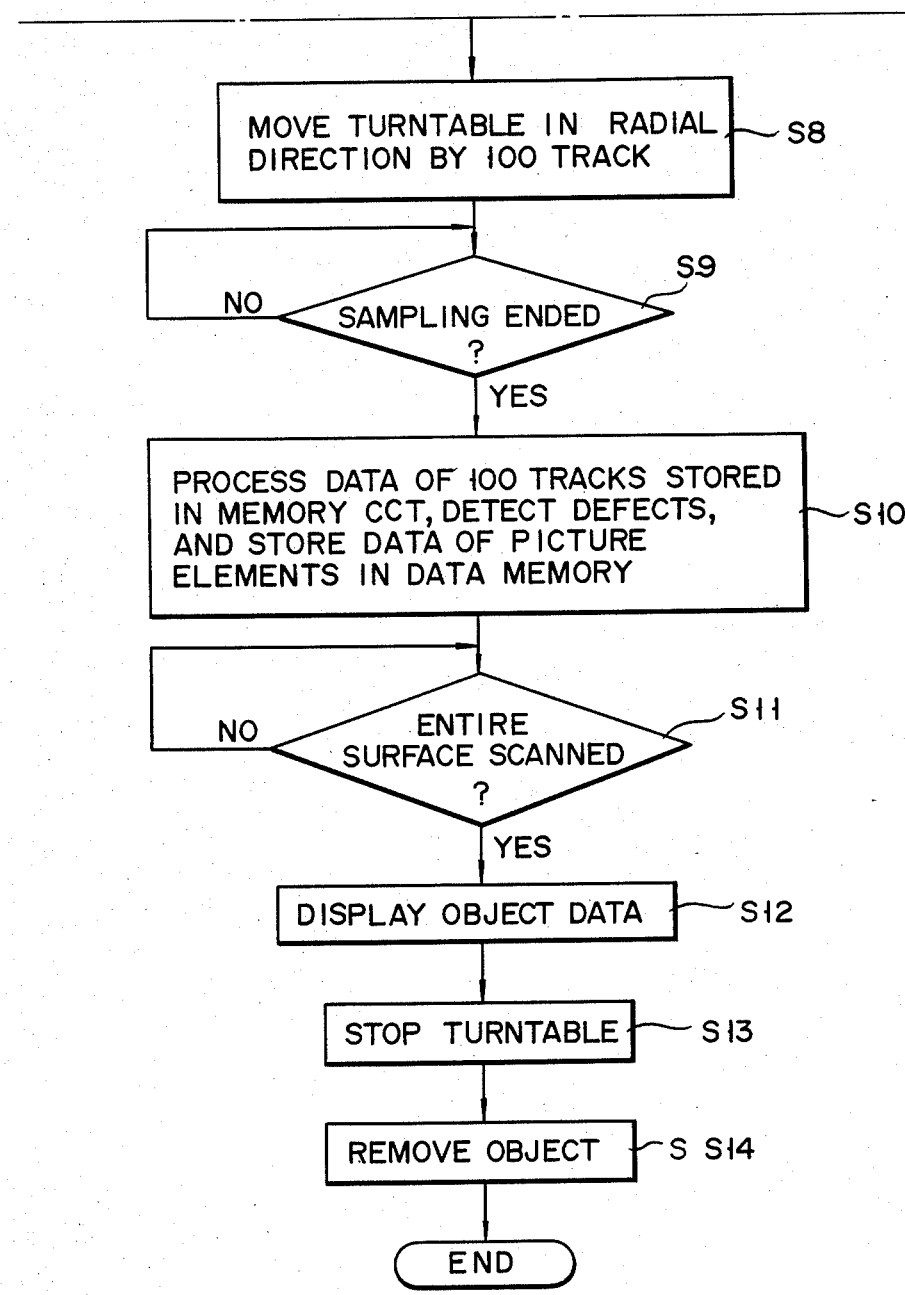

The operation of the surface defect inspecting apparatus thus arranged will be described referring to a flowchart shown in FIGS. 4A and 4B.

The laser light is reformed into a fine spot beam through the lens system 11, so that it is ready for spotting the surface of the object 10. The light collector 13 and the photo-electric converter 14 for detecting the scattered light from the object 10 are also operated so as to be ready for sensing the scattered light. The regular reflecting light component from the object 10 is split by a half-mirror (not shown) disposed between the lens system 11 and the light collector 13, for example. In a step S1, the object 10 is placed on the turntable 16 and fixed thereto by a fixing means (for example, a vacuum chuck). Then, in a step S2, the stepping motor 20 is driven by a signal Cs from the operation control unit 21 applied through the stepping motor control circuit 22. The stepping motor 20 is driven to move the turntable 16 in the radial direction. Then, the turntable 16 is stopped at a position of a specific radius r of the object 10 where it is irradiated with laser beam. In a step S3, the DC motor 18 for rotating the turntable 16 is rotated by a signal $C_D$ from the operation control unit 21. In a step S4, the by-path circuit 26 is driven at the position of the radius r; the output of the A/D converter 24 is directly connected to the memory circuit 27. The output voltage from the photo-electric converter 14 during the period of one turn of the turntable 16 is subjected to A/D conversion. Then, the A/D converted one is written into the memory circuit 27. As the data of one turn of the turntable 16 at the position of the radius r of the object 10 is written into the memory circuit 27, a step S5 is executed where the operation control unit 21 performs the data processing for obtaining threshold levels $T_1$, $T_2$ and $T_3$. To obtain the threshold levels, a mean value $V_A$ of all of the data $(X_1, X_2, \ldots, X_n;$ where $n=100)$ as obtained is calculated by the following equation.

$$V_A = (X_1 + X_2 + X_3 + \ldots X_n)/n$$

Figure 5:
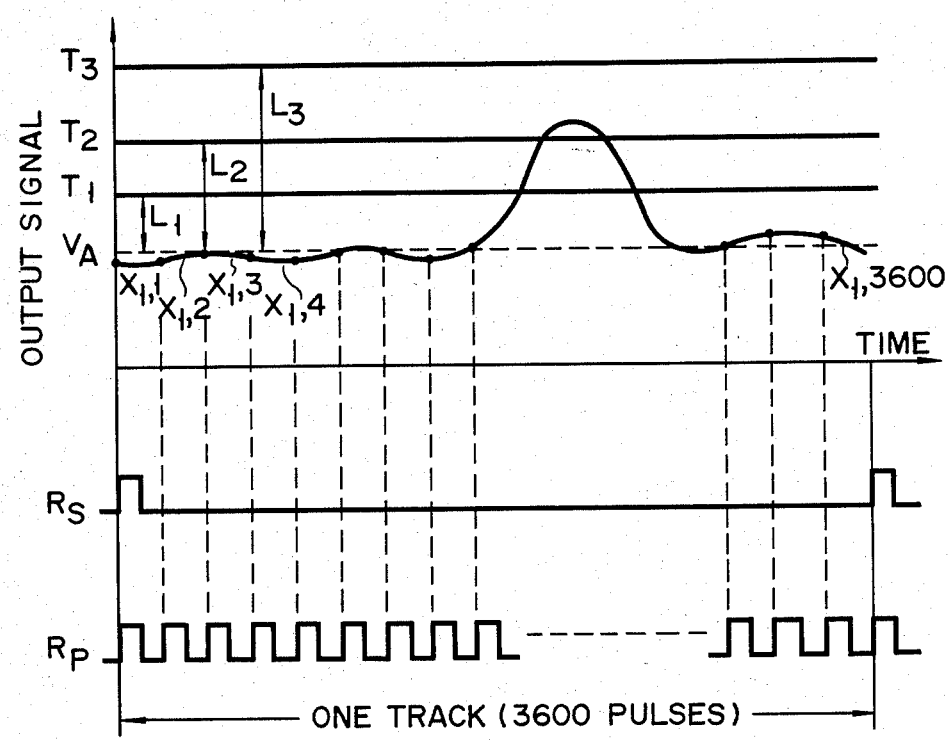
FIG. 5 shows a timing chart of the data sampling by the FIG. 3 embodiment.
Figure 6:
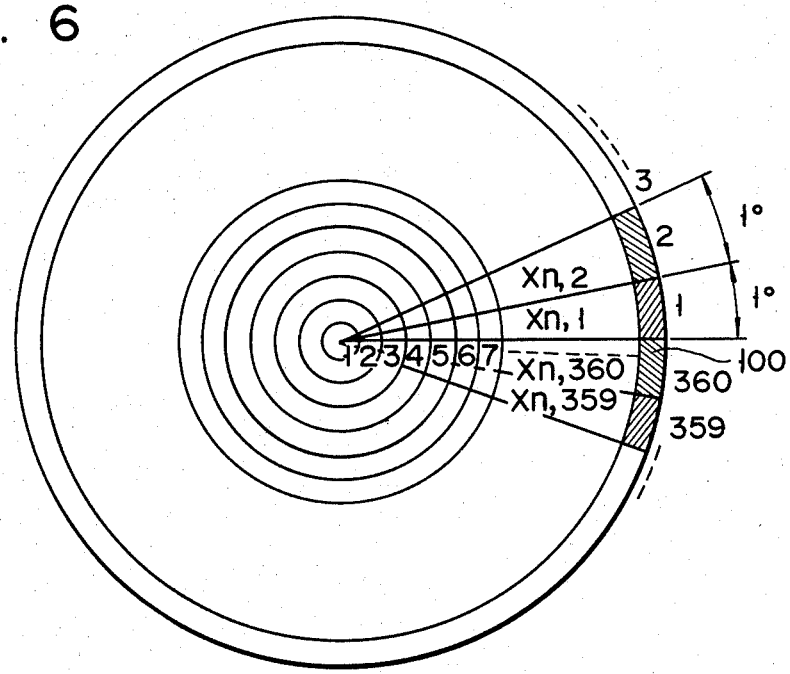
FIG. 6 shows a data sampling area on the surface of an object under inspection, when the FIG. 3 embodiment is applied for the surface defect inspection of the object.

In a step S6, levels $L_1$, $L_2$ and $L_3$ are set up. A mean value $V_A$ is added to the respective levels $L_1$, $L_2$ and $L_3$ to set up the threshold levels $T_1$, $T_2$ and $T_3$. It is assumed that $L_1$ is a level for detecting the smallest surface defect of 1.0 μm or less, as shown in FIG. 5. Then, $T_1$ ($=V_A+L_1$) is a threshold level for detecting the smallest surface defect. Similarly, also in setting the larger surface defect than the above, levels $L_2$ and $L_3$ (where $L_1<L_2<L_3$) are set up. Then, these levels $L_2$ and $L_3$ are added to the mean value $V_A$, thereby to obtain threshold levels $T_2$ and $T_3$. In a step S7, by a signal Cs from the control unit 21, the stepping motor 20 is driven to move the turntable 16 in the radial direction. Then, the turntable 16 is stopped at a position where the center of the object 10 is irradiated with the laser beam. For stopping the turntable 16 at that position, a limit switch is mounted thereat and operated when the limit switch is driven. In a step S8, the by-path circuit 26 is driven to connect the A/D converter 24 to the comparator 25. Then, the DC motor 18 is driven to turn the turntable 16. At this time, for each rotation of the turntable 16, the stepping motor 20 is driven to radially move the turntable 16 track by track, a distance of a total of 100 tracks. The width of the track is 80 to 90% of a spot diameter d of the laser beam, i.e., 0.8 d to 0.9 d. During this operation, the address generating circuit 23 is also driven by a control signal output from the operation control unit 21. The address generating circuit 23 produces an address signal As of a coordinate representing a defect inspecting position on the object, in response to a rotation start signal Rs output from the rotary encoder 19, a rotating position signal Rp and a drive signal output from the stepping motor control circuit 22. In a step S9 for performing a sampling operation, an analog voltage, which is output from the photoelectric converter 14 and varies an intensity of the scattered light, is digitized by the A/D converter 24, every 0.1° in synchronism with the rotating position signal Rp of the rotary encoder 19 directly coupled with the rotary encoder 19. The rotating position signal Rp is a pulse signal and contains 3600 pulses for each rotation. As for the digital data, a maximum of consecutive ten data is taken out by the comparator 25, and output to the memory circuit 27 (see FIG. 6). In synchronism with the address signal As, the scattered light data of 100 tracks are stored into a memory a location with a predetermined address of the memory circuit 27. As a result, the memory circuit 27 stores the maximum data of the scattered light in each area as defined by a center angle of 1°, as shown in FIG. 7. Each maximum data consists of a pair of data Yn and θ (360 data for each rotation × 100 tracks). In a step S10, the data stored in the memory circuit 27 are processed so as to form data in which an area of 10 tracks within 1° of the center angle in FIG. 6 is treated as one picture element. To this end, the data of 100 tracks shown in FIG. 7 are divided into 10 blocks. A maximum value of each block is detected for each rotation, thereby to form the data of one picture element. The operation control unit 21 compares the present data with the threshold levels $T_1$, $T_2$ and $T_3$, and classifies the data on the basis of the size of the surface defects. The classified data is stored into the data memory 29. A sequence of the steps S1 to S10 is repeated. In a step S11, if the entire surface of the object is scanned, the operation control unit 21 advances in the flow of control to a step S12. In this step, the display section 31 visually displays a distribution of surface defects of the object 10 and the number of the surface defects as classified on the basis of the defect size. Such a display by the display section 31 is performed on the basis of the surface defect data from the data memory 29. Then, in a step S13, the turntable 16 is stopped in rotation. In the next step S14, the turntable 16 is returned to a home position. Then, the object 10 is removed from the turntable 16. At this point, the inspecting operation of the object 10 ends.

As seen from the foregoing, the surface defect inspecting apparatus according to the first embodiment of the present invention works out a mean value $V_A$ of the data along a periphery of a circle with the radius r on a location of the surface of the object 10 as properly selected, and a plurality of levels $L_1$ to $L_3$ for detecting the surface defects is added to the mean value $V_A$, thereby to form threshold levels $T_1$ to $T_3$. This is commonly done when different objects are inspected, when the object 10 is warped, and when an intensity of the scattered light from a non-defective place of the object 10 varies. Therefore, there is eliminated the need of calibrating the threshold levels with a reference sample for each object. Therefore, the surface defect inspecting apparatus can qualitatively and accurately detect surface defects of the object. The calculation of the mean value $V_A$ is carried out using part of data not all of the data collected from the surface of the object 10. Additionally, in the surface defect inspecting apparatus according to the first embodiment of the present invention, the data of a plurality of tracks are sampled and stored. Then, the surface defects are detected. Further, the data are blocked for each the picture element. To effect the above, the temporary memory is provided. Therefore, there is no need for storing all of the data collected from the entire surface of the object. This implies that a memory capacity of the memory is saved. Further, in sampling the data, the comparator 25 obtains the maximum values of ten consecutive data. Only the maximum values are automatically stored as effective data into the memory, in synchronism with the signals representative of rotating and tracking positions of the turntable 16. Therefore, the data processing time by the operation control unit 21 is reduced. Further, the number of start and stop operations of the turntable 16 for the data sampling is once for 100 tracks. In this respect, the time for the data sampling is remarkably reduced. Thus, the surface defect inspecting apparatus is applied for inspecting the surface defects of the wafer in manufacturing integrated circuits, inspecting efficiency and accuracy are remarkably improved to greatly contribute to improvements of quality and yield of integrated circuits.

The laser beam used in the above-mentioned embodiment may be replaced by any type of light, if it is optically sensed by the photo-electric converter. The light collector 13 is used for the scattered light sensing in the above-mentioned embodiment, but it may be replaced by any other appropriate means. Further, the number of pulses for each rotation in the rotating position signal of the turntable, that is, 3600 pulses for each rotation, may appropriately be selected. In place of the rotary encoder, the side face of the turntable is marked black and white, and the reflecting light from the black and white marks is used for data collection. In the above-mentioned embodiment, the laser beam is moved from the center of the object to the periphery. The direction of the movement of the laser beam may be reversed. It is sufficient that the object is coaxially scanned by the laser beam. In the above-mentioned embodiment, the calculation of the mean value $V_A$ is performed using the data on one periphery of a circle with the specific radius r on the object 10 surface, which is collected before the actual inspection. Alternatively, for the calculation of the mean value $V_A$, the data on one periphery of the circle with the radius r are selected from the data stored in the memory circuit 27, during an actual inspection. Further, the data on the peripheries of circles with different radii may be collected for the mean value calculation. Additionally, for the mean value $V_A$ calculation, the data of 1000 for example, properly selected from all of the data on the object 10 may be used in place of the data on one periphery. In other words, it is within the scope of the invention that the mean value $V_A$ is calculated using the data properly selected from all of the data on the object 10. In the above-mentioned embodiment, checking presence or not of surface defects is performed after all of the data are stored into the data memory 29. In parallel with storing process of the data into the memory circuit 27, the presence or not of the surface defect may be performed by the operation control unit 21. In the first embodiment as mentioned above, for the data sampling, the maximum values of the 10 consecutive data are obtained. The number of the data may be any one of the numbers of two or more.

Figure 9:
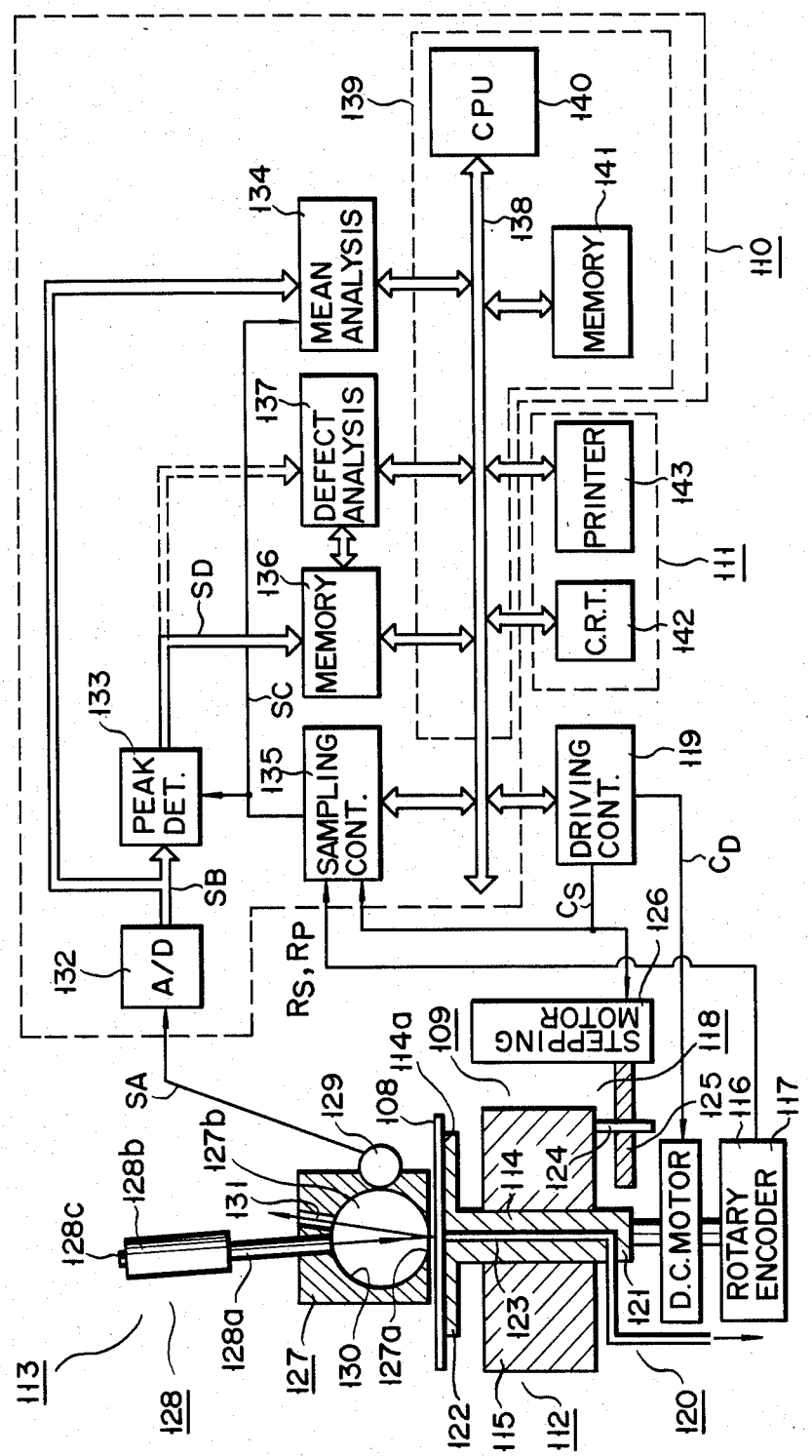
FIG. 9 shows in block form an overall arrangement of a surface defect inspecting apparatus which is a second embodiment of the present invention.
Figure 10:
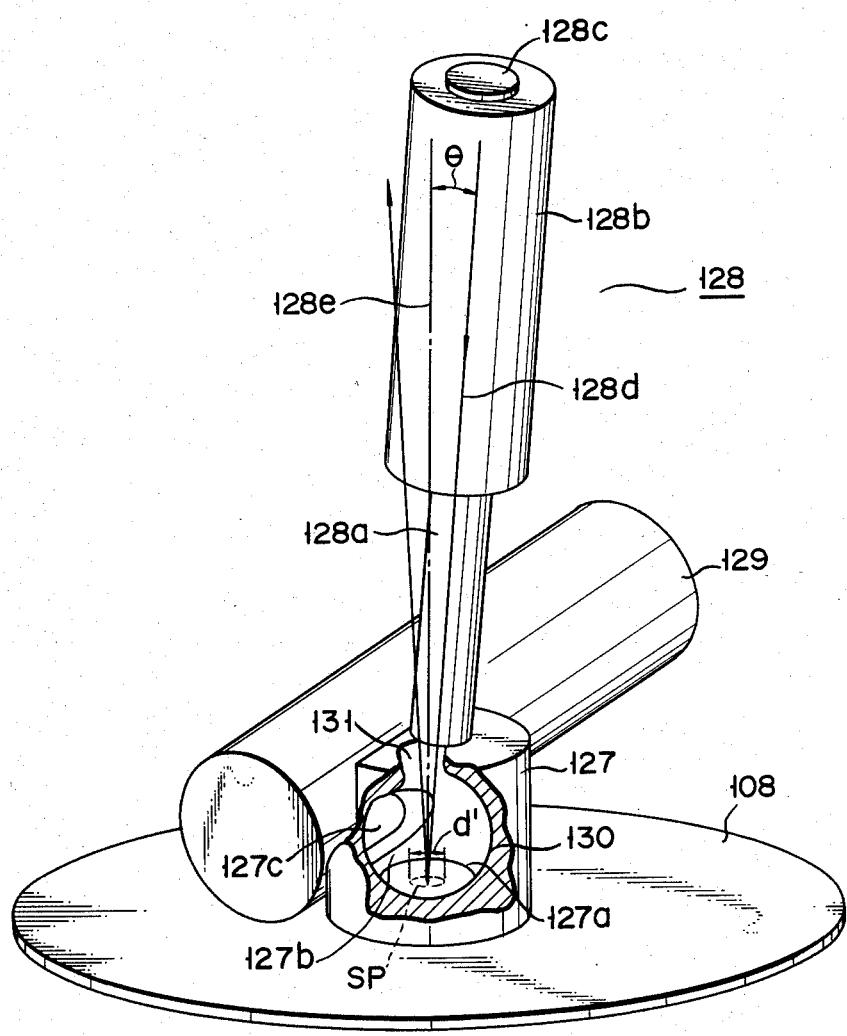
FIG. 10 shows a perspective view of an illuminating section used in the FIG. 9 embodiment.

FIG. 9 shows an arrangement of an overall surface defect inspecting apparatus which is a second embodiment of the present invention. The surface defect inspecting apparatus is comprised of a scanning mechanism 109 for illuminating with laser beam an object under inspection 108 as shaped like a disc, such as a semiconductor wafer, a signal processing section 110 for detecting surface defects of the object 108 using a signal output from the scanning mechanism 109, and a signal processing section 111 for visually displaying the result of inspection. The scanning mechanism 109 is comprised of a holder 112 for holding the object 108, and an illuminating section 113 for illuminating the object 108 held by the holder 112 with laser beam. The holder 112 is comprised of a turntable 114 on which the object 108 is coaxially placed, a bearing member 115 for rotatably supporting the turntable 114, a first motor 116 for rotating the turntable 114 supported by the bearing member 115, a rotary encoder 117 for detecting a rotation of the turntable 114 directly coupled with the first motor 116, a feeding section 118 for moving the bearing member 115 coupled with the bearing member 115 in the radial direction of the object 108 and in a retractible manner, a drive control section 119, and a sucking section 120 for sucking the object 108 on the turntable 114. The drive control section 119 controls the feeding section 118 and the first motor 116 to turn the object 108 placed on the turntable 114 by a predetermined amount of turn. The turntable 114 is comprised of a disc like shaft 121, and a disc-like table 122 of which the upper surface coaxially coupled with the upper end of the shaft 121 serves as a suction face 114a for the object 108. The suction face 114a has a suction hole 123 as a part of the sucking section 120. The suction hole 123 axially passes through the shaft 121, and is coupled with a vacuum source (not shown) through a rotary joint (not shown) from the lower side of the shaft 121. The feeding section 118 is comprised of a plate 124 suspending from the lower end of the bearing member 115, a feed screw 125 screwed into the plate 124 and having an axial directed in the radial direction of the shaft 121, and a second motor 126. The second motor 126 is directly coupled with one end of the feed screw 125 and rotates the feed screw 125 to move the turntable 114 in the direction and in a retractible manner. The first and second motors 116 and 126 are rotated by a predetermined amount of turn in response to control signal CD and CS derived from the drive control section 119. The illuminating section 113 is comprised of a spherical integrating light collector 127, a laser source 128 and a photo-electric converter 129, as shown in FIG. 10. The spherical integrating light collector 127 is cylindrical and is disposed so as to be close to the object 108 fixed to the suction face 114a. The light collector 127 is provided with a spherical hollowed section 127b which has a circular opening 127a at the lower end. The laser source 128 is coupled at one end with the spherical integrating light collector 127, and obliquely projects laser beam on the object 108, through an opening 127a of the spherical integrating light collector 127. The photo-electric converter 129 is coupled with the spherical integrating light collector 127 directly or through an optical fiber (not shown), and receives the scattered laser beam as reflected from the object 108 and collected by the spherical integrating light collector 127, and converts the scattered light into an electrical signal. A photomultiplier, a photo transistor, a photo diode, or the like may be used for the photo-electric converter 129. The inner surface of the spherical integrating light collector 127 is coated with magnesium oxide to form a diffusion surface 130. The upper portion of the spherical integrating light collector 127 is provided with a through-hole 131 allowing the regular reflecting light from the object 108 to pass through to exterior. The spherical integrating light collector 127 is also provided with a window 127c. A light sensing portion of the photo-electric converter 129 is fitted to the window 127c. The laser source 128 is comprised of a cylindrical optical path member 128a which is connected at one end with the spherical integrating light collector 127 and communicates with a hollowed section 127b of the light collector 127, a cylindrical diaphragm 128b coaxially coupled at one end with the other end of the optical path member 128a, and a laser device 128c mounted to the other end of the diaphragm 128b. The diaphragm 128b contains an optical system (not shown) for diaphragming the laser beam output from the laser device 128c. An optical axis 128d of the laser beam as set up by the diaphragm 128b is selected to be oblique to a normal 128e of the object 108 at an angle $\theta$. The axial line of a through-hole 131 is selected to be oblique to the normal 128e at an angle $\theta$. Therefore, the laser beam generated by the laser device 128c is obliquely incident on the object 108 along the optical axis 128d. The regular reflecting light passes through the through-hole 131 to exterior. The signal processing section 110 is comprised of the signal processing section 110, an A/D converter 132, a peak detector 133, a mean value calculating unit 134, a sampling control section 135, a first memory section 136, a surface defect classifying section 137, and a central processing section 139. The A/D converter 132 converts an analog signal output from the photo-electric converter 129 into a digital signal. The peak detector 133 detects a peak value of the digital signal output from the A/D converter 132. The mean value calculating unit 134 calculates a mean value of the digital signal output from the A/D converter 132. The sampling control section 135 is connected at the input to the rotary encoder 117 and the drive control section 119, and at the output to the peak detector 133 and the mean value calculating unit 134. The sampling control section 135 produces a sync signal for sampling the digital signal derived from the A/D converter 132 in the peak detector 133 and the mean value calculating unit 134. The first memory section 136 stores a digital signal representing a peak value output from the peak detector 133. The surface defect classifying section 137 receives the digital signal of the peak value output from the first memory section 136, detects the surface defect, and classifies the surface defect on the basis of the size of the defects. The central processing section 139 is connected through a system bus 138 the mean value calculating unit 134, the sampling control section 135, the surface defect classifying section 137, the first memory section 136, the drive control section 119 and the display section 111, and systematically controls those circuit sections according to a predetermined measuring program. The central processing section 139 includes a CPU 140 as a microcomputer for executing various arithmetic operations and controls, and a second memory 141 for controlling a control program for performing an object surface inspection according to a predetermined sequence of procedural steps and the results of inspection. The mean value calculated by the mean value calculating unit 134 is set up as a plurality of threshold levels. This is done by the surface defect classifying section 137 in response to a command issued by the CPU 140 and applied through the system bus 138. The surface defect classifying section 137 compares the plurality of threshold levels with the peak value output from the peak detector 133. Through the comparison, the surface defect data is extracted for each defect size, and the number of the defect data is counted. The display section 111 includes a display 142 and a printer 143. The display 142 contains a cathode ray tube (CRT), reads out the inspection result data from the surface defect classifying section 137, and displays a distribution of the surface defects on the object surface, and the number of the defects for each defect size.

Figure 11A:
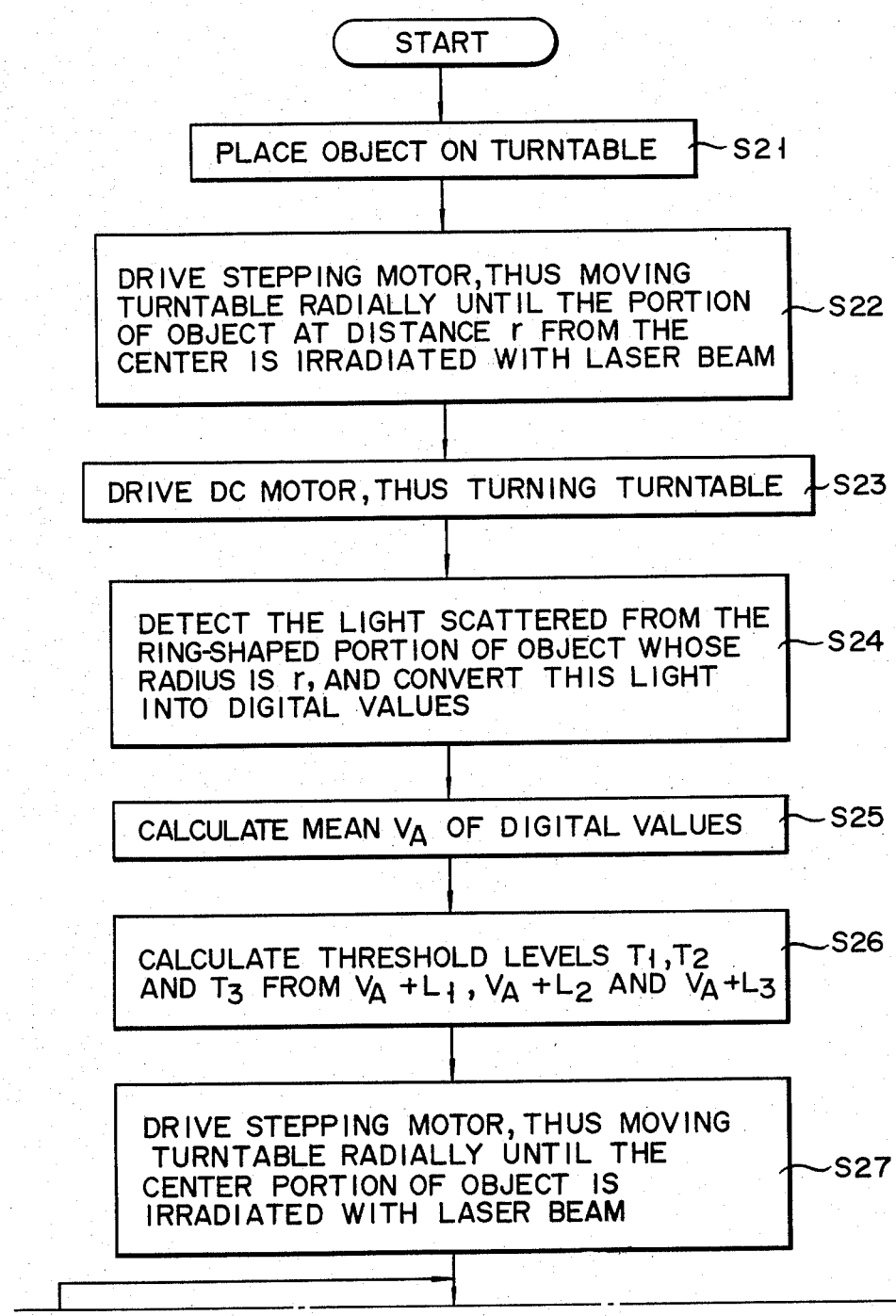
FIGS. 11A and 11B cooperatively chart flow of operations of the FIG. 9 embodiment.
Figure 11B:
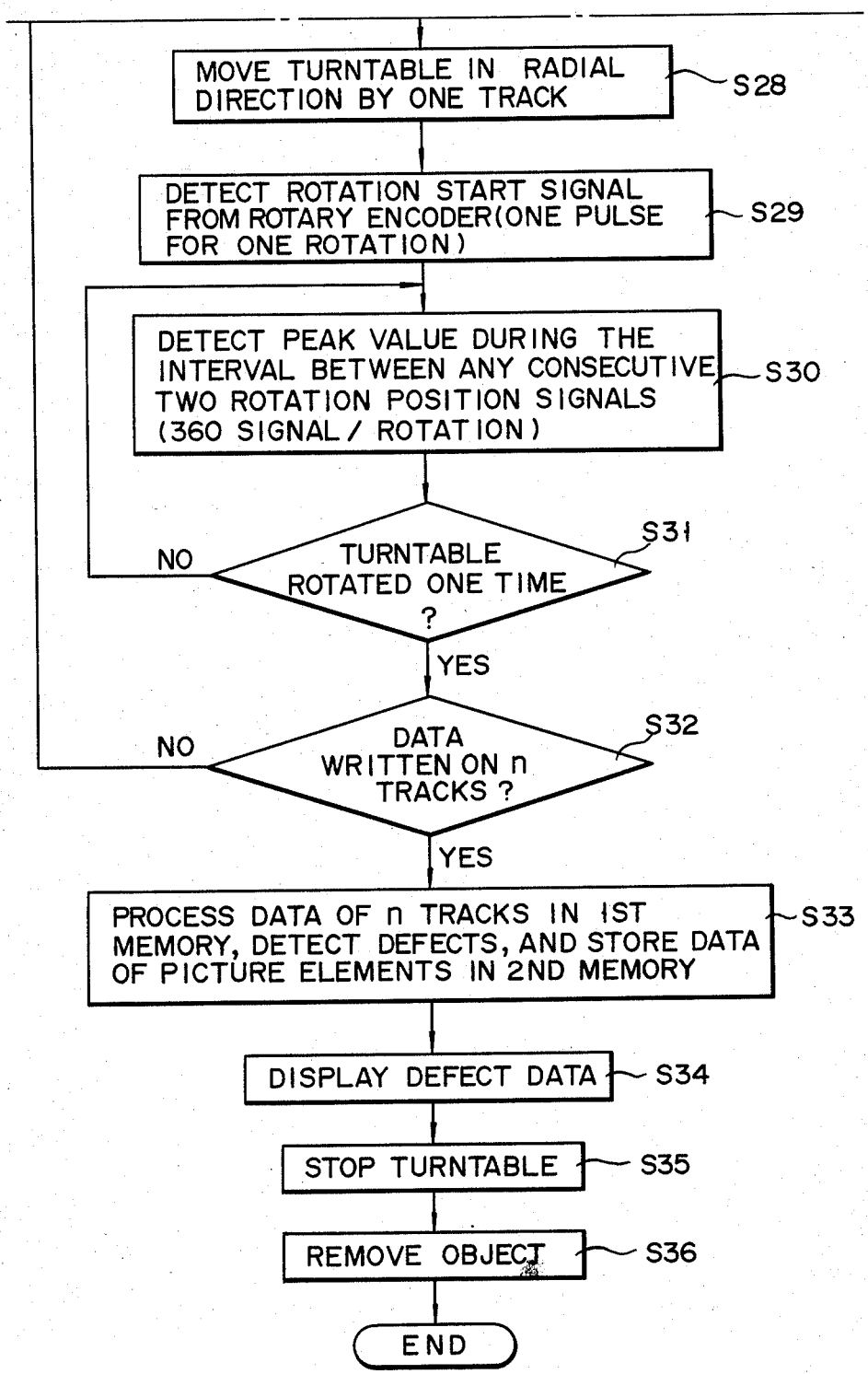

The operation of the surface defect inspecting apparatus thus arranged will be described referring to a flowchart shown in FIGS. 11A and 11B.

Figure 12:
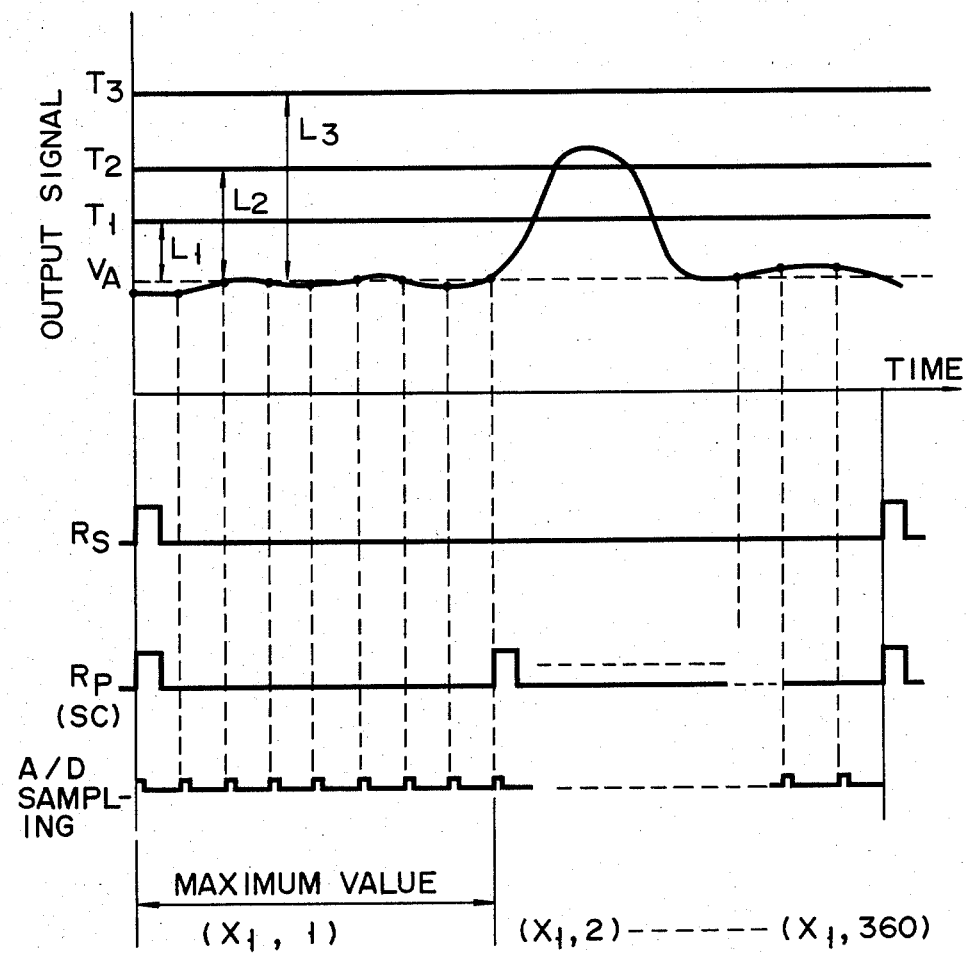
FIG. 12 shows a timing chart of the data sampling performed by the FIG. 9 embodiment.
Figures 13, 14:
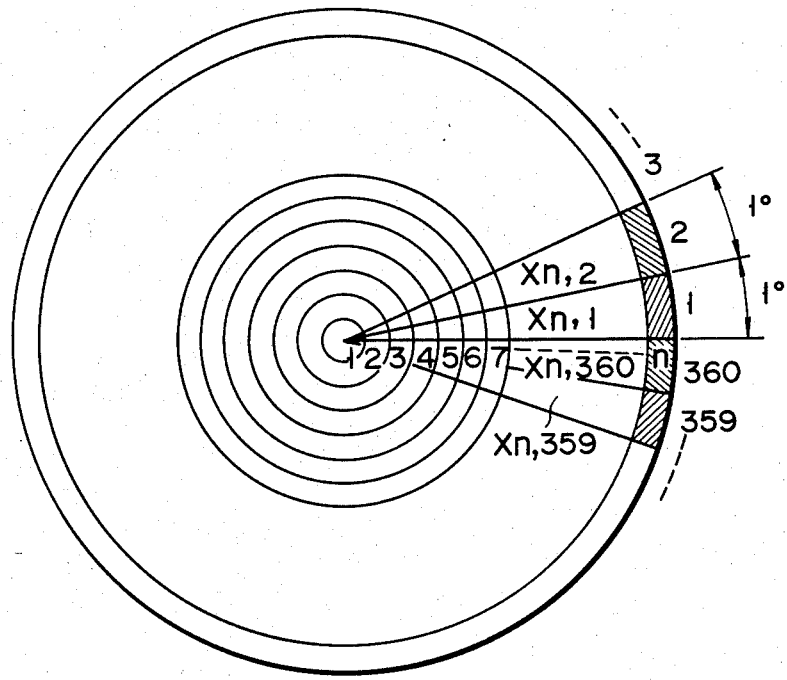
FIG. 13 shows a data sampling area on the surface of an object under inspection, when the FIG. 9 embodiment is applied for the surface defect inspection.
FIG. 14 maps an arrangement of data stored in a temporary memory in the FIG. 9 embodiment.

The laser beam is set so that it projects an elliptical spot on the object 108, through the diaphragm 128b. The regular reflecting laser beam from the object 108 is emitted outside through the through-hole 131. At this time, the major axis of the elliptical spot SP of the laser beam is orthogonal to the scanning direction of the object 108 (the peripheral direction), that is, it is set so as to widen the scanning width. The scattered laser beams are collected by the diffusion surface 130. Further the spherical integrating light collector 127 for collecting the scattered light and the photo-electric converter 129 are set so as to be ready for the inspection. In a step S21, the object 108 is placed on the table 122 and fixed thereto by the sucking section 120. In a step S22, the second motor 126 is driven by the signal Cs from the drive control section 119, through the rotation of the feed screw 125, and is moved in the radial direction. The table 122 is stopped at a position where the laser beam is projected on a position of the radius r of a circle properly set at the central portion on the object 108. In a step S23, the first motor 116 for rotating the table 122 is driven by the signal $C_D$ from the drive control section 119. Then, the object 108 is rotated by ten rotations. During this period, the photo-electric converter 129 produces an analog sensing signal analog detecting signal SA proportional to an amount of the received light for transfer to the A/D converter 132. In a step S24, the mean value calculating unit 134 A/D converts the sensing signal analog detecting signal SA, and applies the converted signal SB to the mean value calculating unit 134. At the start of rotation of the table 122, the rotary encoder 117 produces during the rotation, a rotation start signal Rs and a rotating position signal Rp (360 pulses/rotation) representing a rotating position for transfer to the sampling control section 135. Then, the sampling control section 135 produces on the basis of the signals rotation start signal Rs and rotating position signal R, a sampling signal SC corresponding to the rotation of the table 122 for transfer to the mean value calculating unit 134. The sampling signal SC is a pulse signal which contains 360 pulse for each rotation of the table 122. Therefore, in a step S25, by the mean value calculating unit 134, the sensing signal SB is stored in synchronism with the sampling signal SC. Then, the arithmetic mean value $V_A$ of all of the data $(X_1, X_2, \ldots, X_n)$ thus obtained is calculated. In the next step S26, the mean value $V_A$ is temporarily stored in the second memory 141. Then, the CPU 140 adds the levels $L_1$–$L_3$ as preset in the second memory 141 corresponding to the size of the surface defects such as dust and scratch to the mean value $V_A$, thereby to provide the threshold levels $T_1$–$T_3$. For example, as shown in FIG. 12, then smallest surface defect (10 $\mu$m or less) is $L_1$ and then $T_1(=V_A+L_1)$ is a threshold level for detecting the surface defect. Similarly, also in detecting the surface defect larger than the above, the levels $L_2$ and $L_3$ (where $L_1<L_2<L_3$) are set up. These levels $L_2$ and $L_3$ are added to the mean value $V_A$, thereby to provide threshold levels $T_2$ and $T_3$. Then, the threshold levels $T_1$ to $T_3$ are transferred via the system bus 138 to the surface defect classifying section 137 and set therein. In a step S27, the second motor 126 is driven by the signal Cs from the drive control section 119 to radially move the table 122. Then, the table 122 is stopped at a position where the laser beam irradiates the center of the object 108. Such a position is detected by a limit switch (not shown). In a step S28, the second motor 126 is driven to move the table 122 by one track in the radial direction. At this time, one track is set at 80–90% of the major axis d' of the elliptical spot of the laser light, that is, (0.8 to 0.9)×d'. In a step S29, the table 122 is turned in the above-mentioned manner. Then, the rotary encoder 117 produces a rotation start signal Rs output at the start of rotation of the table 122, and a rotating position signal Rp containing 360 pulses for each rotation of the table 122. These signals rotation start signal Rs and rotating position signal Rp are supplied to the sampling control section 135. Upon receipt of these signals, the sampling control section 135 applies a sampling signal SC containing 360 pulses for each rotation to the peak detector 133. In the A/D converter 132, analog detecting signal analog detecting signal SA output from the photo-electric converter 129 is digitized into a detecting signal SB. The SB is applied to the peak detector 133. The peak detector 133 obtains a peak value for each period of the sampling signal SC in synchronism with the sampling signal as input. The peak signals detecting signal SD representing the peak values are sequentially applied to the first memory section 136 and stored in predetermined memory locations therein. In a step S31, the data (360 data) of one turn of the table 122 is loaded into the first memory section 136. Then, the table 122 is further moved by one track in the radial direction. Again, the one turn data is loaded into the memory, by the sampling signal SC. In a step S32, a predetermined number n of tracks are scanned in this way. The peak value data $(Xn, \theta)$ are stored in the first memory section 136, as shown in FIG. 14. For collecting the peak value data from the object 108, the object 108 is segmented into a number of fan-shaped areas by coaxially dividing the object surface and angularly dividing the same by 1°, as shown in FIG. 13. In a step S33, the first memory section 136 produces a digital signal representing the peak value data (Xn, $\theta$) and applies the signal to the surface defect classifying section 137. Then, the surface defect classifying section 137 classifies the surface defects on the basis of the defect size, using the threshold level $T_1$ to $T_3$ as already set. For detecting the smallest surface defect of 1.0 μm or less, all of the data are successively compared with the threshold level $T_1(=V_A+L_1)$. The data larger than the threshold level $T_1$ are treated as the surface defect data. For detecting the surface defects larger than the above, all of the data are successively compared with the threshold level $T_2(=V_A+L_2)$, and the threshold level $T_3(=V_A+L_3)$. The data larger than the threshold levels $T_2$ and $T_3$ are treated as the defect data. Further the defect data thus obtained are classified depending on the defect size. In a step S34, the CPU 140 converts the polar coordinates into the Cartesian coordinates, and calculates to find what number of the surface defects are contained in the picture element of 1 mm×1 mm. The CPU 140 further drives the display section 111 to display a distribution of the surface defects on the Cartesian coordinates as converted and the number of the surface defects for each defect size. In the display by the display section 111, if a plurality of the surface defects are contained in one picture element, the largest surface defect is representatively displayed as the defect data of the picture element. Finally, in a step S35, the rotation of the table 122 is stopped, and in the next step S36, the table 122 is returned to the home position. Then, the object under inspection is removed from the table 122. At this point, the inspection work ends.

As described above, the surface defect inspecting apparatus according to the second embodiment of the present invention works out a mean value $V_A$ of the data along a periphery of a circle with the radius r on a location of the surface of the object 108 as properly selected, and a plurality of levels $L_1$ to $L_3$ for detecting the surface defects are added to the mean value $V_A$, thereby to form threshold levels $T_1$ to $T_3$. This is commonly done when different object are inspected, when the object 108 is warped, and when an intensity of the scattered light from a non-defective place of the object 108 varies. Therefore, there is eliminated the need of calibrating the threshold levels with a reference sample for each object. Therefore, the surface defect inspecting apparatus can qualitatively and accurately detect surface defects of the object. The calculation of the mean value $V_A$ is carried out using part of data, not all of the data, collected from the surface of the object 108. Additionally, in the surface defect inspecting apparatus according to the present invention, the data of a plurality of tracks are sampled and stored. Then, the surface defects are detected. Further, the data are blocked for each the picture element. To effect the above, the temporary memory is provided. Therefore, there is no need for storing all of the data collected from the entire surface of the object. This implies that a memory capacity of the memory is saved. When a semiconductor device is used for the laser source, the following effects can be obtained. (1) Approximately 15 mW of the laser output can be obtained. Therefore, an intensity of the scattered light from the object is enough to provide a high sensitivity for the surface defects. (2) It is allowed to assemble a power control circuit for keeping the optical output constant into the surface defect inspecting apparatus. Therefore, there is eliminated an output variation mainly due to the aging, which is inevitable for the He-Ne laser device. Accordingly, a stability of the inspection is improved. (3) The laser beam emitted from the semiconductor laser device expands to have an elliptical cross section of which the major axis is aligned with the vertical direction, not the vertical direction. Therefore, an elliptical beam can easily be obtained not using a complicated optical system. This implies that a scanning width of the laser beam is wider than that of the circular beam, and the scanning time for scanning the object can be reduced. (4) Since the semiconductor laser device is smaller in size than the He-Ne laser device, and its power source is smaller than that of the later. It is possible to reduce the illuminating section in size and weight. This feature lessens space occupied by the laser device in a clean room.

360 pulses per one turn of the turntable in the rotating position signal may be changed to the proper number of pulses for each turn, if necessary. For the calculation of the mean value $V_A$, the data is detected at the position of a circle of a specific radius r on the object 108, which are collected before an actual inspection. The data collected on the positions of a plurality of radii may be used for the calculation.

In the above-mentioned embodiment, the peak value data from the peak detector 133 derived from the peak detector 133 are temporarily stored in the first memory section 136. Alternatively, as indicated by a broken line in FIG. 9, the peak signal SD is directly applied to the surface defect classifying section 137. In the surface defect classifying section 137, the surface defects are classified in a real time manner. The classified data are loaded into the first memory section 136 or the second memory 141. When the surface defect inspecting apparatus of the present invention is applied for the wafer surface inspecting step in manufacturing integrating circuits, the inspecting work is improved in efficiency and accuracy, and hence the integrated circuits manufactured are improved in quality and production yield.

Figure 15:
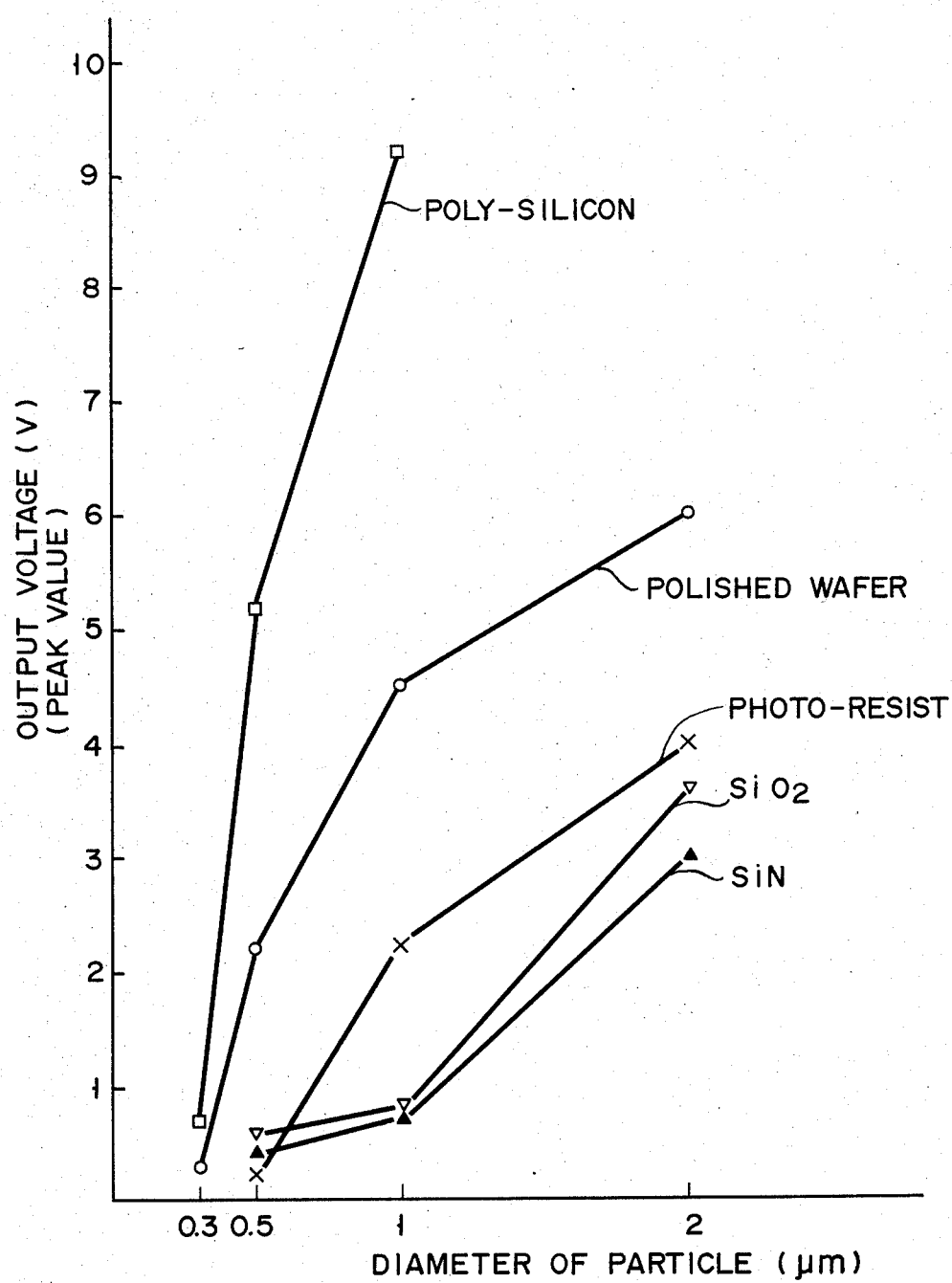
FIG. 15 shows a sensitivity evaluation curve useful in explaining modifications of the first and second embodiments.

In the first and second embodiments as mentioned above, for setting necessary threshold levels, each of the levels $L_1$–$L_3$, for example, is added to the mean value $V_A$ automatically obtained for each object. Alternatively, the levels $L_1$–$L_3$ may be changed for each object under inspection. As seen from FIG. 15 illustrating a detecting sensitivity of the surface defect inspecting apparatus when the object is only the polished wafer, it is different from that when the object is a wafer with a film of SiN, $SiO_2$, photo-resist, or polycrystalline silicon. In this case, levels ($L_{1i}$, $L_{2i}$ and $L_{3i}$) are prepared and stored in the data memory 29 or the second memory 141. These levels are read out according to the mean value $V_A$ as obtained or by means of a plurality of operation keys.

Figure 16:
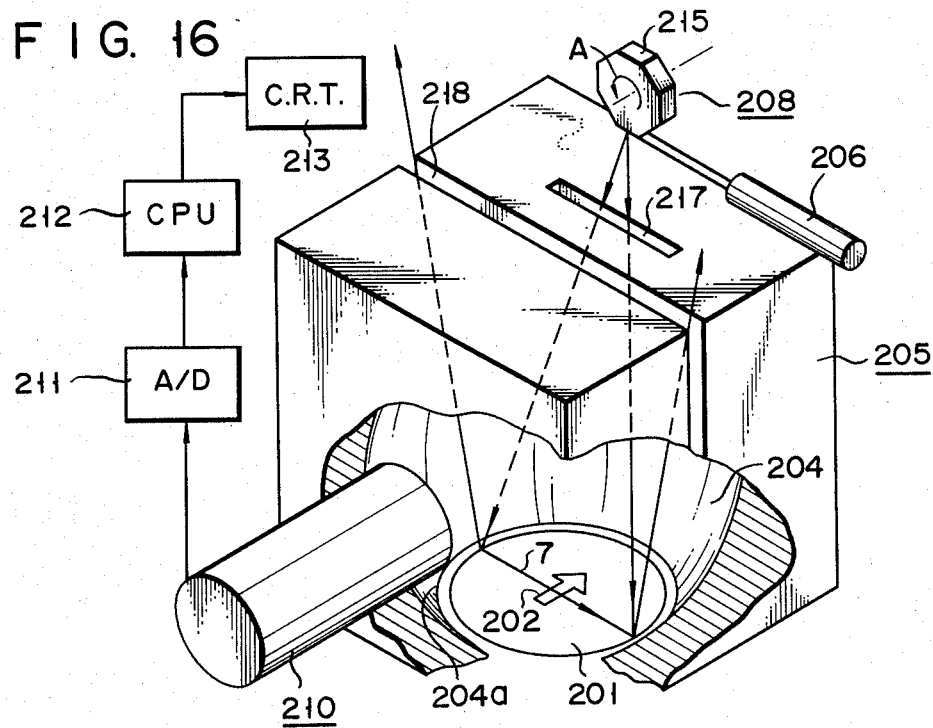
FIG. 16 shows a perspective view, partially broken, of a third embodiment of a surface defect inspecting apparatus according to the present invention.
Figure 17:
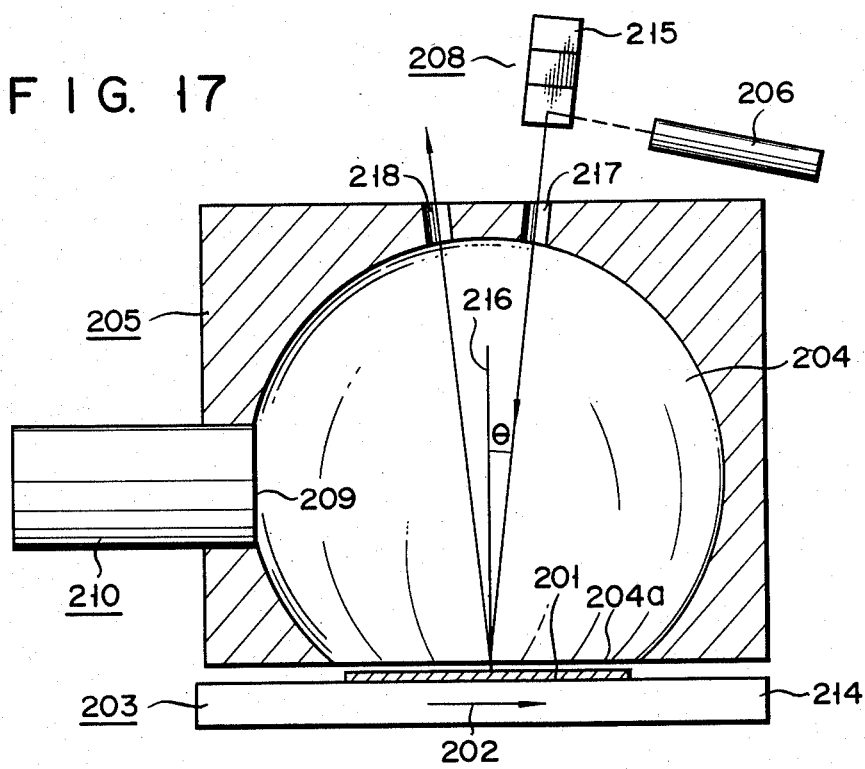
FIG. 17 shows a cross sectional view of a surface defect inspecting apparatus shown in FIG. 16.

FIGS. 16 and 17 show a third embodiment of a surface defect inspecting apparatus according to the present invention. As shown, the surface defect inspecting apparatus is comprised of an object placing means 203, a spherical integrating light collector 205, a light source 206, an optical deflecting section 208, a photo-electric converter 210, a A/D converter 211, a data processing unit 212, and a display section 213. The object placing means 203 is rectilinearly moved in the direction of arrow 202, while bearing thereon a wafer 201 as an object under inspection. The light collector 205 has a hollowed section 204 for collecting the scattered laser beam as is reflected at the wafer right above the object placing means 203. The light source 206 generates laser beams. The optical deflecting section 208 reflects the laser beam emitted from the light source 206 and moves the laser beam in the direction of arrow 207 orthogonal to the direction of arrow 202, thereby to scan the wafer 201. The photo-electric converter 210 is provided with a light receiving surface 209 as a part of the surface of the hollowed section 204. The photo-electric converter 210 produces an electrical signal representing an amount of the light received by the light receiving surface 209. A photomultiplier, a photo diode, a photo transistor or the like, may be used for the photo-electric converter 210. The A/D converter 211 A/D converts the electrical signal from the photo-electric converter 210. The data processing unit 212, such as a microcomputer, arithmetically processes the digital signals output from the A/D converter 211 under control of a program preset in a proper memory, and checks the present or not of defects on the wafer surface. This is like that of the first and second embodiments. The display section 213 visually displays the results of defect checking by the data processing unit 212. The object placing means 203 includes a table 214 on which a wafer 201 is placed at a predetermined location thereon, and a drive mechanism (not shown) for moving the table 214 at a constant speed in the direction of arrow 202, and may be a stepping motor. A hollowed section 204 opens at the under surface of the light collector 205. The hollowed section 204 has an opening 204a which is circular with an outer diameter slightly larger than the outer diameter of the wafer 201. The inner surface of the hollowed section 204 is coated with magnesium oxide or barium sulfate, thereby to form a diffusion surface. The optical deflecting section 208 includes a rotating polygonal mirror 215 and a rotating drive mechanism (not shown) for rotating the rotating polygonal mirror 215. The rotating axis of the rotating polygonal mirror 215 is arranged in such a manner that the laser beam reflected by the rotating polygonal mirror 215 moves for scan at the maximum diameter portion of the opening 204a in the direction of arrow 207, and at an angle $\theta$ with respect to the normal upstanding on the major surface of the wafer 201. More specifically, a plane through which laser beam reflected by the rotating polygonal mirror 215 passes (this plane is orthogonal to the rotating axis of the rotating polygonal mirror 215) is slanted at an angle $\theta$ with respect to a plane containing the normal line on the major surface of the wafer in the direction of arrow 207, or the scanning locus, and in the scanning direction at the center of the opening 204a. The number of the reflecting faces of the rotating polygonal mirror 215 is so selected that the scanning distance is equal to the inner diameter of the opening 204a. Such a number is, for example, 18. The light source 206 contains a laser oscillator. An optical axis of the laser beam oscillated in and emitted from the light source 206 is normal to a line parallel to the rotating axis of the rotating polygonal mirror 215, while satisfying the scanning condition on the major surface of the wafer 201. An incoming slit 217 provides a path through which the laser beam reflected by the rotating polygonal mirror 215 enters into the hollowed section 204. An outgoing slit 218, crossing the light collector 205 at the substantially center thereof, provides a path through which the laser beam has scanned the wafer surface. Only the regular reflecting light is led to exterior. The incoming slit 217 and the outgoing slit 218 are disposed symmetrically with respect to the surface 216.

The operation of the surface defect inspecting apparatus thus arranged will be described.

The wafer 201 is placed on the turntable 214. The object placing means 203 is driven to position the wafer 201 at the location closer to one's side than the center line of the opening 204a. In synchronism with the control signal from the data processing unit 212, the drive mechanism feeds the table 214 at 400 mm/sec in the direction of arrow 202. Then, the laser beam is emitted from the light source 206. The rotating drive mechanism in the optical deflecting section 208 is driven to rotate the rotating polygonal mirror 215 at 3600 turns/min. in the direction of arrow A. Then, the laser beam from the light source 206 is deflected by the rotating polygonal mirror 215, and reaches the upper surface of the table 214 through the incoming slit 217. The laser beam at the upper surface of the table 214 is moved for scan at the maximum diameter portion of the opening 204a in the direction of arrow 207. When the leading end of the wafer 201 as being fed by the drive mechanism of the object placing means 203 reaches the center of the opening 204a, the wafer 201 is scanned by the laser beam at a high speed in the direction of arrow 207. In this way, the wafer 201 is successively scanned from the leading and trailing ends, while being moved in the direction of arrow 202. Finally, the wafer 201 is entirely scanned on the surface by the laser beam. During this scanning operation, of the laser beams reflected by the wafer 201, the regular reflecting laser beams are led to exterior completely. When the wafer surface has defects such as dust particles or scratch, the reflecting laser beams contain scattered reflecting laser beams. The scattered reflecting light is collected, by the inner surface of the opening 204a as the scattered reflecting surface, onto the light receiving surface 209. Then, it is converted into an electrical signal containing an amount of the received light, by the photo-electric converter 210. The electrical signal output from the photo-electric converter 210 is digitized by the A/D converter 211 and stored into the data processing unit 212. In the data processing unit 212, the data are stored with an array corresponding to the coordinates applied to the wafer surface illuminated with the laser beam. Each data is arithmetically processed for surface defect inspection. For example, in the first and second embodiments as mentioned above, each data is compared with a preset threshold level. The data having a voltage level higher than the threshold level is treated as the data representing a defective position on the wafer surface, and is displayed by the display section 213.

As seen from the foregoing, in this embodiment, the wafer surface is scanned at a high speed by the laser beam through the optical deflecting section 208. At the same time, the object placing means 203 bearing the wafer 201 is moved in the direction orthogonal to the scanning direction. Therefore, the entire surface of the wafer 201 can be scanned at high speed and high accuracy. Use of the spherical integrating light collector collects only the scattering light due to the surface defect. The thus collected light is used for surface defect detection. This remarkably improves a sensitivity of defect detection.

While in the third embodiment, the photo-electric converter 210 is directly coupled with the light collector 205, one end of the optical fiber is exposed toward the inner surface of the opening 204a, while the other end thereof is coupled with the photo-electric converter provided separately from the light collector 205. A normal light source, in place of the laser source, may be used for the light source 206. The rotating polygonal mirror 215 in the optical deflecting section 208 may be any optical means if it can move the laser beam at high speed, such as a galvano-mirror. The moving direction of the object placing means 203 is not necessarily normal to the laser-moving direction, the direction of arrow 207. Alternatively, for the scanning, the object placing means 203 is fixed, while the light source 206, the optical deflecting section 208 and the light collector 205 are kept in a fixed positional relation.

What is claimed is:

1. An apparatus for inspecting an object under inspection for defects on the surface thereof, comprising:
   means for holding the object under inspection in a manner that the substantially entire surface of the object may relatively be scanned by laser beam;
   spherical integrating light collecting means provided at one end with an opening disposed close to the inspected surface of the object held by said holding means;
   laser beam illustrating means coupled with another end of said spherical integrating light collecting means and for illuminating said inspected surface of the object with the laser beam through said opening;
   photo-electric converting means for receiving the scattered light as is reflected by said inspected surface and collected by said spherical integrating light collecting means, and for converting the scattered light into an electrical signal representing an amount of light;
   analog to digital converting means for analog to digital converting the electrical signal derived from said photo-electric converting means into a digital signal;
   peak detecting means for receiving the digital signal derived from said analog to digital converting means to detect peak values at predetermined periods;
   means for calculating a mean value based on a digital signal output from said analog to digital converting means;
   means for storing at least one reference value which is for determining at least one threshold level to detect surface defect or defects present on said inspected surface;
   means for calculating said threshold level based on said reference value and said mean value; and
   surface defect detecting means for comparing peak values derived from said peak detecting means with said threshold level, and for detecting the surface defect or defects depending on the result of the comparison.

2. The apparatus according to claim 1, further comprising means for detecting a position signal corresponding to said relative scanning.

3. The apparatus according to claim 2, in which said analog to digital converting means performs an analog to digital conversion according to said position signal.

4. The apparatus according to claim 2, in which said peak value detecting means detects peak values in response to said position signal.

5. The apparatus according to claim 2, in which said mean value calculating means calculates a mean value according to said position signal.

6. The apparatus according to claim 1, in which said holding means includes a turntable on which said object is put on, a first motor for rotating said turntable, and a second motor for moving said turntable in its radial direction.

7. The apparatus according to claim 1, in which said holding means includes an object placing means containing a table which is rectilinearly moved in the first direction, bearing said object thereon.

8. The apparatus according to claim 7, in which said laser illuminating means includes an optical deflecting section which allows the laser beam to illuminate said inspected surface while being moved in a second direction orthogonal to said first direction.

9. The apparatus according to claim 1, in which said spherical integrating light collecting means is coupled with said laser illuminating means at a position where said laser beam is allowed to illuminate said object at a predetermined angle with respect to the normal line of said inspected surface of said object, and said spherical integrating light collecting means is provided with light passing means through which the regular reflecting component from said inspected surface is conducted exteriorly of said collecting means.

10. The apparatus according to claim 1, in which said laser illuminating means includes a semiconductor laser device.

11. The apparatus according to claim 10, in which a major axis of an elliptical spot on said inspected surface is orthogonal to said scanning direction, said elliptical spot being formed by the laser beam emitted from said semiconductor laser device.

12. The apparatus according to claim 1, in which said photo-electric converting means is directly coupled with said spherical integrating light collecting means.

13. The apparatus according to claim 1, in which said photo-electric converting means is provided separately from said spherical integrating light collecting means.

14. The apparatus according to claim 1, in which said mean value calculating means calculates a mean value based on said digital signal corresponding to a part of said inspected surface, which said digital signal is obtained before an actual inspection.

15. The apparatus according to claim 1, in which said mean value calculating means calculates a mean value based on a predetermined digital signal selected from the digital signals corresponding to said inspected surface, which are obtained in an actual inspection.

16. The apparatus according to claim 1, in which said reference value storing means stores a plurality of reference values corresponding to sizes of the surface defects to be inspected.

17. The apparatus according to claim 1, in which said reference value storing means stores a plurality of reference values which are respectively different for objects to be inspected.

18. The apparatus according to claim 1, in which said surface defect detecting means processes said peak values extracted through a temporary memory from said peak detecting means.

19. The apparatus according to claim 1, in which said surface defect detecting means processes said peak values directly extracted from said peak detecting means, in a real time.

* * * * *